United States Patent [19]

Baldock

[11] Patent Number: 4,838,094

[45] Date of Patent: Jun. 13, 1989

[54] GRAIN SAMPLE APPARATUS

[76] Inventor: Donald V. Baldock, Cummings, N. Dak. 58223

[21] Appl. No.: 32,020

[22] Filed: Mar. 30, 1987

[51] Int. Cl.$^4$ .............................................. G01N 1/20
[52] U.S. Cl. .............................. 73/863.81; 73/864.64
[58] Field of Search .......... 73/863.31, 863.33, 863.81, 73/864.51, 864.64; 222/173, 180–181, 185, 464, 434, 436–437, 439

[56] References Cited

U.S. PATENT DOCUMENTS

| | | | |
|---|---|---|---|
| 840,943 | 1/1907 | Ingold | 73/863.33 |
| 985,329 | 2/1911 | Decremer | 222/439 |
| 2,675,706 | 4/1954 | Edgar | 73/863.33 |
| 2,694,931 | 11/1954 | Handley | 73/863.31 |
| 2,702,475 | 2/1955 | Dougherty et al. | 73/863.33 X |
| 3,065,637 | 11/1962 | Landes | 73/863.31 |
| 4,574,645 | 3/1986 | Allen et al. | 73/863.51 |
| 4,625,570 | 12/1986 | Witherspoon et al. | 73/863.81 |

FOREIGN PATENT DOCUMENTS 390403  11/1973  U.S.S.R. ............................ 73/863.81

*Primary Examiner*—Michael S. Huppert
*Attorney, Agent, or Firm*—Robert E. Kleve

[57] ABSTRACT

The invention comprises a grain sampling device installed in a grain bin. The apparatus has a plurality of sleeves in concentric relation, with the upper ends of the sleeves adjacent the upper central portion of the bin so as to be beneath and close to the top of the grain pile when the grain pile substantially fills the grain bin. The sleeves extend downward from the top central portion at an angle and project out the wall of the bin near the bottom of the bin. Lateral pipe sections are mounted to the inner sleeve on the outside of the bin so as to serve as handles and outlets and the sleeves have openings at selected levels inside the bin including the top of the sleeves whereby by rotation of the handles from outside the bin the openings in the sleeves can align with one another at selected levels to allow grain in the bin at the selected level to gravitate into the inner sleeve through the openings and travel under a gravitational flow downward along the inner sleeve outside the bin and out a lateral section to enable a sample of grain to be obtained.

4 Claims, 2 Drawing Sheets

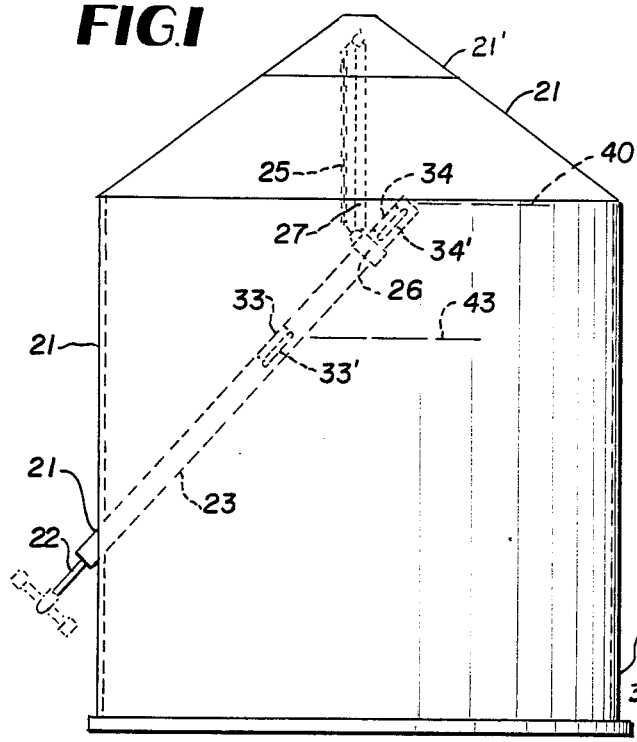
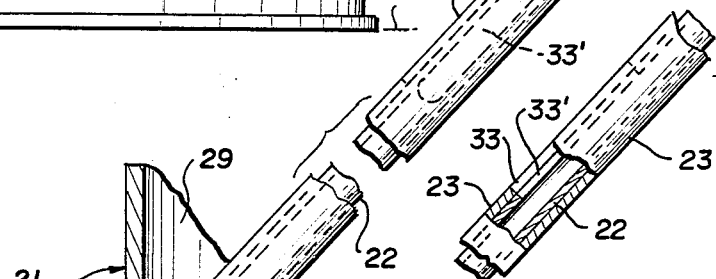
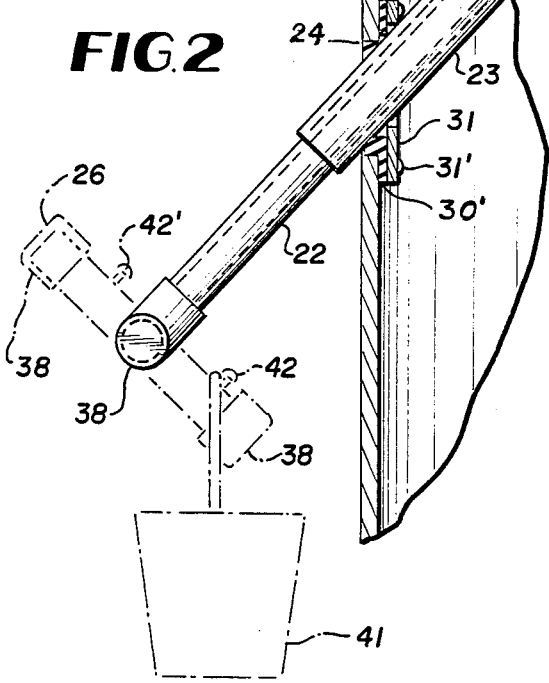

FIG.4
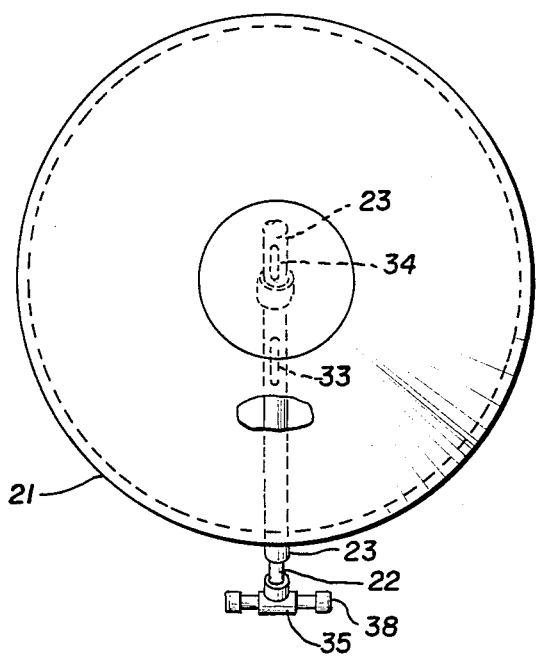
FIG.5
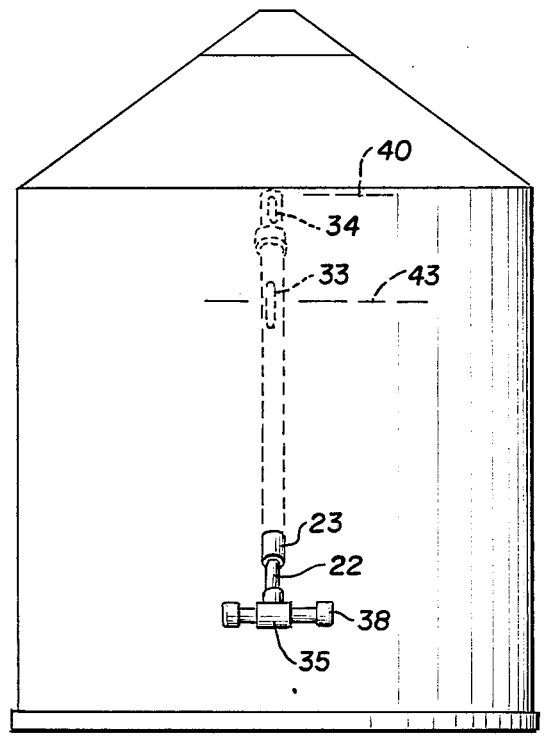
FIG.6 FIG.7
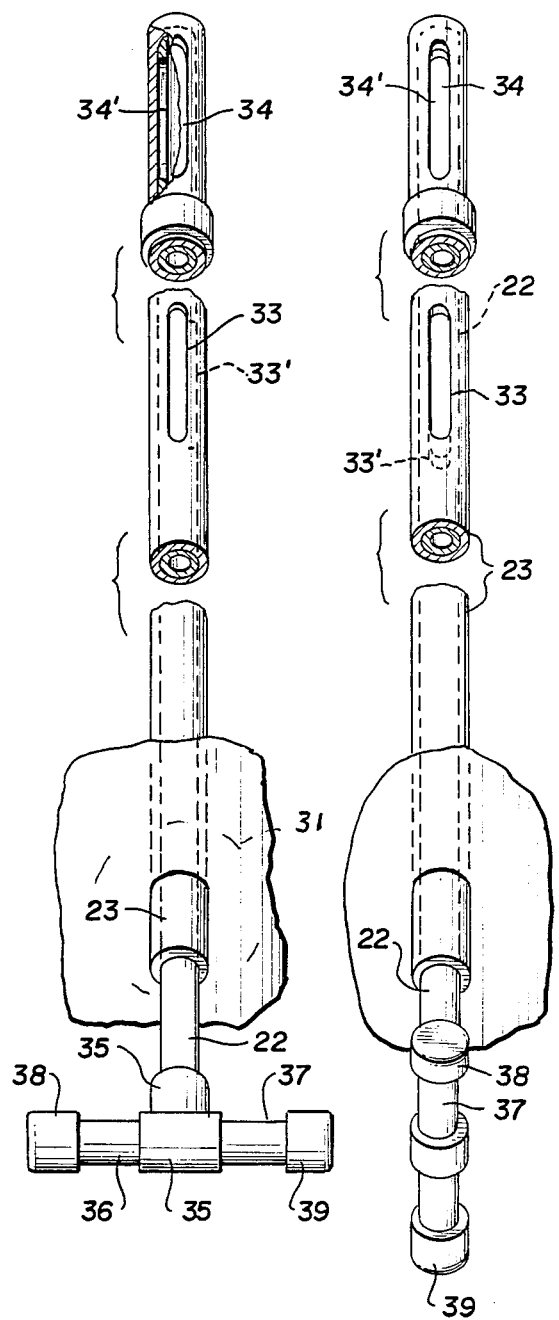

GRAIN SAMPLE APPARATUS

This invention relates to grain sampling and inspection devices and the like.

It is an object of the invention to provide a novel grain sampling device which can convey grain from within the interior of a grain bin to the exterior of the bin.

It is a further object of the invention to provide a novel grain sampling apparatus which can be installed in a grain bin and which feeds a sample of grain from within the bin near the top of the grain when it substantially fills the bin to the exterior of the bin near the bottom of the bin by gravity flow.

It is another object of the invention to provide a novel grain sampling apparatus which can be used to obtain a grain sample of grain stored within a bin at selected levels in the stored grain and convey it to the exterior of the bin where the sample can be used for evaluation.

Further objects and advantages of the invention will become apparent as the description proceeds and when taken in conjunction with the accompanying drawings wherein:

FIG. 1 is a side elevational view of the grain conveying sleeve apparatus in a grain bin for taking a sample of grain therein.

FIG. 2 is an enlarged fragmentary side elevational view of the grain conveying sleeve sampling apparatus.

FIG. 3 is side view similar to FIG. 2 with the inner sleeve turned 90 degrees from FIG. 2 counterclockwise when viewing the sleeves from the exterior of the bin looking toward the bin to place the intermediate inner opening in alignment with the intermediate outer opening.

FIG. 4 is a top plan view of the grain conveying sleeve apparatus in a grain bin.

FIG. 5 is an enlarged fragmentary front view of the grain conveying sleeve apparatus, shown with the inner sleeve shown in it closed position.

FIG. 6 is an enlarged fragmentary front view of the grain conveying sleeve apparatus, with the inner sleeve shown in one of its closed positions.

FIG. 7 is an enlarged fragmentary front view of the grain conveying sleeve apparatus, with the inner sleeve shown in one of its open positions.

Briefly stated, the invention comprises a grain conveying sleeve apparatus for installation in a grain bin for sampling the grain in the bin. The sleeve apparatus has a pair of elongated plastic tubes or sleeves mounted in concentric relation with the inner tube rotatably mounted to the outer tube. The upper ends of the tubes are mounted near the top and center of the grain bin so as to be beneath and adjacent the top of a grain pile when the grain pile is in a bin and substantially fills the bin. The tubes are mounted so as to extend from near the top and center of the bin a downward at an angle toward the exterior of the bin near the bottom of the bin with the lower ends of the tubes extending outward from the wall of the bin. The inner tube has lateral sections fixed to the lower ends of the inner tube to serve as handles to rotate the inner tube relative to the outer tube and an exterior outlet for the inner tube. The tubes have openings at selected levels so that the rotation of the inner tube will align the inner tube openings with the outer tube openings at the selected level to allow grain to gravitate into the aligned openings into the inner tube and gravitate down the inner tube and out the outlet of the inner tube for use as a sample of the grain at that level.

Referring more particularly to the drawings, in FIG. 1 the grain conveying sleeve apparatus 20 for sampling grain is shown mounted or installed in a grain bin 21. The sleeve conveying apparatus has elongated tubes 22 and 23 of plastic mounted in concentric relation to one another. The tubes are mounted in the bin to extend upward at an angle from the lower exterior of the bin, through an opening 24 in the bin 21 toward the top and center of the bin. The bin 21 has a conventional removable cap 21'. A chain 25 is attached to its upper end to the removable cap and extends downward with its lower end attached to an eyelet on a clasp 26 which clasp surrounds and is fixed to the upper end portion 28 of the sleeve 23. A coil spring 27 also have its upper end attached to the removable cap and extends downward with its lower end attached to the eyelet on the clasp 26. The coil spring serves as a sole support and a resilient cushion for the upper ends of the sleeves 22 and 23. The chain is normally loose and serves as a limiting means to limit the downward movement of the sleeves in relation to the cap.

The lower ends of the sleeves 22 and 23 extend through an opening 24 in the wall 29 of the bin at a location near the ground 30. The outer sleeve has a resilient rubber sleeve 30' that surrounds the sleeve 23 in the opening 24 to seal the space between the opening in the wall 24 and the exterior of the outer sleeve 23. A metal circular plate 31 is fixed to the interior of the wall 29 by bolts 31' and engages an annular ridge on the resilient sleeve to force the sleeve into the space 24 so as to more completely seal the opening 24.

The plastic sleeves 22 and 23 have slots 33 and 33' respectively, intermediate the height of the sleeves and a pair of slots 34 and 34', respectively, at the upper ends of the sleeves. The slots 33 and 34 in the sleeve or pipe 23 are at the intermediate level and upper end of the pipe or sleeve and are aligned arcuately in the same degree relation to one another along the top fo the tube. The slots 33' and 34' of the sleeve or pipe 22 are at the same intermediate height and upper end height locations on pipe 22 as the slots 33 and 34, however, the slots 33' and 34' are positioned arcuately 180 degrees from one another, so that the rotation of the pipe 22 in pipe 23 may place slot 33' of pipe 22 in alignment with slot 33 of pipe 23, while slot 34' of pipe 22 is out of alignment with slot 34 of pipe 23, so that the grain can travel into the inner sleeve or pipe only at the intermediate level 43 of slots 33 and 33'.

The inner sleeve 23 can be rotated 180 degrees from the alignment position of slots 33 and 33' which will place the slots 34 and 34' of sleeves 22 and 23 respectively in alignment near the top of the sleeves and will place the slots 33 and 33' of the sleeves out of alignment, so that grain can travel into the inner sleeve or pipe only at the upper end of the sleeves 22 and 23.

A T-shaped tubular connection 35 has one end 35' fitted over the lower end of sleeve 22. A pair of tubular sections 36 and 37 are fixed in the outer opposing ends of the T-shaped connection 35. A pair of plastic caps 38 and 39 are fitted over the outer ends of sleeve sections 36 and 37 for opening and closing the ends of sleeves sections 36 and 37 and thereby open and close the lower end of sleeve 22.

OPERATION

The tubular conveying apparatus 20 is operated when an operator desires to obtain a sample of grain, at one or more levels within the grain bin while on the ground adjacent the outside of the bin.

When the grain substantially fills the grain bin 21 to the customary level 40 and it is desired to obtain a sample of this grain at this level 40' near the top to determine the quality and condition of the grain near the top; the operator, without having for example to climb to the top of the bin and obtain a sample via the removal cover, will rotate the inner sleeve 22 relative to the outer sleeve 23 to move the sleeve from one of its closed positions illustrated in FIG. 6 to its position shown in FIG. 7, by grasping the handle sections 36 and 37 and rotating sleeve 22 approximately 90 degrees to align the slot 34' of the inner sleeve with the slot 34 of the outer sleeve. When these two slots align with one another the handle sections 36 and 37 and sleeves will be in their vertical position shown in FIG. 7.

When the slots 34 and 34' are in alignment with one another, grain from the grain pile near the top 40' can travel into the sleeves through the slots 34 and 34' into sleeve 22 under gravitational flow and travel downward, under gravitational flow along the interior of sleeve 22 and out of the lower end of sleeve 22 and into the T connection and gravitate out the lateral pipe section 37.

A pail 41 can be attached by its handle to the screw 42 on the pipe section 37 as illustrated in FIG. 2 and the cap 38 removed so that the grain sample, from within the bin near the top of the grain pile that gravitated down sleeve 22 and out section 37 can travel into the pail 41.

Since when slots 34 and 34' are in alignment with one another slots 33 and 33' are out of alignment the grain will enter the sleeve 22 only through slots 34 and 34'.

If it is desired to obtain a sample of grain from within the grain bin at an intermediate height 43, intermediate the height of the grain bin and grain pile at the level of slots 33 and 33' in pipe 22 and 23 respectively, the operator will grasp the handle sections 36 and 37 and rotate the sleeve 22 180° from its position illustrated in FIG. 7 to place the slots 33 and 33' in alignment. This action also moves the slots 34 and 34' out of alignment with one another so that grain cannot enter through slots 34 and 34' and can only enter the sleeves through slots 33 and 33', so that grain at this level can gravitate through slots 33 and 33' into sleeve 22 and gravitate downward along the interior of sleeve 22 out of sleeve 22 into the T connection and through pipe section 36 and out pipe section 36.

The pail 41 can be similarly positioned beneath the pipe section 36 by attaching its handle to the screw 42' and remove the cap 39 to allow grain received in the sleeve from slots 34 and 34' to travel out of section 37 into the pail, so that a sample of grain in the grain bin at the height 43 can be easily obtained from outside the bin on the ground.

When the handle sections 36 and 37 are in their horizontal position illustrated in FIG. 6 or in their horizontal position 180 degrees from their position shown in FIG. 6, the slots 33 and 33', and 34 and 34' are not in alignment with one another so that no grain can enter the sleeves at eight level of any of the slots and the slots in effect the closed.

Thus it will be seen that a novel grain sampling device has been provided which enables a sample of grain to be obtained from a grain pile that substantially fills a grain bin, from outside the grain bin while on the ground, either at locations near the top of the grain pile or intermediate the height of the grain pile and bin easily and quickly by the rotation of the handle on the apparatus from outside the bin and the sample will be conveyed outside the bin.

Additional openings in the sleeves may be placed at different heights in the outer sleeve and at the same different heights only at different arcuate intervals on the inner sleeve, for example, to enable to be rotated to openings into the sleeves at different locations to obtain samples at additional locations or levels in the grain pile in the grain bin if desired.

It will be obvious that various changes and departures may be made to the invention without departing from the spirit and scope thereof, and accordingly, it is not intended that the invention be limited to that specifically described in the specification or as illustrated in the drawings but only as set forth in the appended claims wherein:

What is claimed is:

1. A grain conveying apparatus in combination with a grain bin having a base and an upright cylindrical wall, said apparatus comprising an inner and outer elongated sleeve, said inner sleeve having its lower end rotatably mounted to the wall of the bin with its lowermost end projecting out through the cylindrical wall to the exterior surface of the wall thereof, handle means on said lowermost end of the inner sleeve to rotate the inner sleeve relative to the outer sleeve and wall of the bin, said sleeves being inclined upward relative to the bin with their upper ends near the top of the bin, means connecting said upper ends of the sleeves with the bin to support the sleeves in their inclined position, said outer sleeve having an opening near the top, said inner sleeve having an opening in the top thereof in a position whereby the inner sleeve may be rotated to one position relative to the outer sleeve to align the openings relative to one another, said inner sleeve having an opening in its lowermost end which is exterior to said bin, cap means to close said lower opening, whereby grain may be filled into the bin to near the top of the bin above the openings in the upper end of the sleeves and said handle may be rotated to rotate said upper opening in said inner sleeve relative to said upper opening in said outer sleeve to align the openings to allow grain to gravitate into the upper openings of the sleeves and through the inner sleeve and out the lower opening in the inner sleeve on the exterior of the wall of the bin for obtaining a sample of the grain in the bin near the top of the bin.

2. A grain conveying apparatus according to claim 1 wherein said inner and outer sleeves have intermediate openings intermediate the upper openings and lowermost opening, with the intermediate openings in the respective sleeves at the same level relative to one another but with one of the intermediate openings at a different interval about the circumference of the sleeves than one of the upper openings so that the intermediate openings may be aligned with one another to receive grain in the openings when the openings at the top of the sleeve are out of alignment, by rotation of the handle means, said handle means comprising a lateral pipe connected laterally to and in communication with the lower opening of the inner sleeve with the end of the lateral pipe having an opening for obtaining a sample of grain from the inner sleeve.

3. A grain conveying apparatus in combination with a grain bin having a horizontal base and an upright wall surrounding said base, said conveying apparatus having an elongated inner and outer sleeve with one of said sleeves being rotatable relative to the other, said sleeves being mounted at an inclined angle within said bin with a majority of the inclined sleeves within said bin and with a minor portion of the rotatable sleeve at its lower end projecting out of the upright wall of the bin and rotatably mounted to said bin, handle means mounted on said minor portion of the rotatable sleeve located exteriorly of the bin for rotating said sleeve, said rotatable sleeve having an opening in its lower end on the exterior of the bin with removable cap means for opening and closing said opening, means to attach one of said sleeves at its upper end to the bin near the top of the bin with said upper end of said one sleeve within said bin, said inner and outer sleeves having slots at least near the top of the sleeves whereby rotation of the rotatable sleeve may align the slot in the rotatable sleeve with the slot in the other sleeve so that when the bin is filled with grain to near the top of the bin and above the level of the slots, the grain may enter into the slots into the inner sleeve and travel, under gravity flow, along the inner sleeve downward through the inner sleeve and out the wall of the bin to the exterior of the bin and out through said opening in said rotatable sleeve, when said cap is removed from said opening, for obtaining a sample of the grain within the bin from near the top of the bin to a location on the exterior of the bin.

4. A grain conveying apparatus according to claim 3 wherein said means to attach one of said sleeves to the bin near the top of the bin includes resilient means having one end attached to said one sleeve and its other end attached to said bin near the top of the bin to resiliently secure the sleeves at their upper ends to the bin, and means being provided for limiting the resilient movement of the sleeves relative to the bin.

* * * * *